United States Patent [19]

Neubauer et al.

[11] Patent Number: 5,255,692
[45] Date of Patent: Oct. 26, 1993

[54] SUBCOSTAL PATCH ELECTRODE

[75] Inventors: Heinz Neubauer, Järfälla; Staffan Bowald, Almunge; Jakub Hirschberg, Täby, all of Sweden

[73] Assignee: Siemens Aktiengesellschaft, Munich, Fed. Rep. of Germany

[21] Appl. No.: 940,542

[22] Filed: Sep. 4, 1992

[51] Int. Cl.⁵ ............................................. A61N 1/04
[52] U.S. Cl. ................................. 607/122; 128/642
[58] Field of Search ............ 128/642, 784, 785, 419 D

[56] References Cited

U.S. PATENT DOCUMENTS

| | | | |
|---|---|---|---|
| Re. 27,757 | 2/1970 | Mirowski | 128/419 D |
| 3,942,536 | 3/1976 | Mirowski et al. | 128/419 D |
| 4,030,509 | 6/1977 | Heilman et al. | 128/419 D |
| 4,291,707 | 9/1981 | Heilman et al. | 128/784 |
| 4,662,377 | 5/1987 | Heilman et al. | 128/919 D |
| 5,042,463 | 8/1991 | Lekholm | 128/784 |
| 5,105,826 | 4/1992 | Smits et al. | 128/784 |

*Primary Examiner*—Lee S. Cohen
*Assistant Examiner*—Jeffrey R. Jastrzab
*Attorney, Agent, or Firm*—Hill, Steadman & Simpson

[57] ABSTRACT

An electrode for implantation in a patient and for connection through a lead to a heart stimulation/sensing system has an active electrode element of conductive material and the electrode has a shape and size conforming to an interspace between the periost and the bone at the inner side of a rib proximal to the heart of a patient so as to accommodate location of the electrode at the interspace. The electrode has fixing elements to fix the relative position of the electrode with respect to the rib. An implantation method is also disclosed.

21 Claims, 3 Drawing Sheets

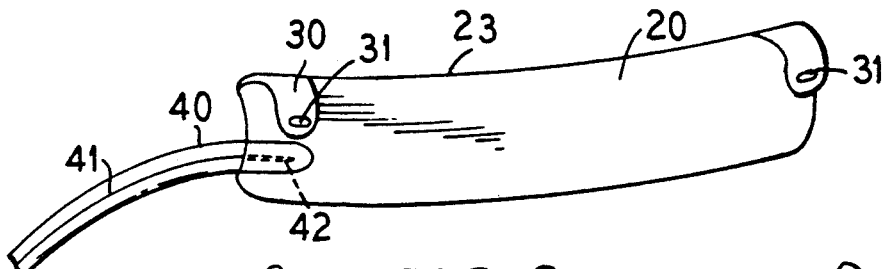
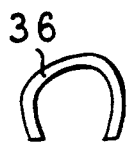
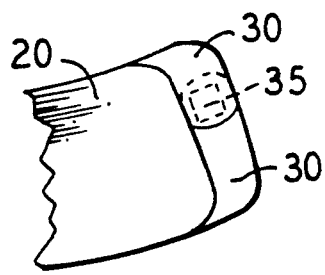

SUBCOSTAL PATCH ELECTRODE

BACKGROUND OF THE INVENTION

1. Background of the Invention

The present invention generally relates to medical electrical stimulation/sensing electrodes. More specifically, the invention is concerned with a large conductive area electrode located subcostally outside the chest cavity and utilized in connection with other electrodes in an implantable cardioverter/defibrillator (ICD or AICD) system for delivering an electrical shock to the heart. These other electrodes may be located externally or internally with respect to the vascular system.

2. Description of the Prior Art

An electrode with a large conductive area located external to the heart is commonly referred to as a patch electrode in the art. As is known, a patch electrode may be of various forms and shapes, i.e., conductive disk or a planar or cup-like conductive mesh. However, when used in its broad sense, the term patch electrode identifies an electrode distinct from an intravascular type electrode, such as a helical or braid electrode.

Cardioverter/defibrillator systems may employ a variety of electrode configurations, such as the entirely epicardial patch electrode system disclosed in U.S. Pat. No. 4,030,509 or the entirely intravascular electrode system disclosed in U.S. Pat. No. 3,942,536. The entirely intravascular catheter electrode arrangement requires relatively high energies to defibrillate the heart and is, even with high energies, not capable of defibrillating the heart in some patients. Thus, while such a system avoids the necessity of surgically opening the chest cavity to implant the electrodes, as is required with epicardially located electrodes requiring relatively low defibrillating energy, an additional patch electrode must be used to reduce the energy required for defibrillation. In order to leave the chest cavity intact, this additional patch electrode is commonly located subcutaneously, outside the rib cage.

One example of an electrode configuration in which a patch electrode is combined with intravascular electrodes is disclosed in U.S. Pat. No. 4,662,377. In this known arrangement, a flexible, subcutaneously placed patch electrode (positioned between the rib cage and the skin) is electrically connected to a first intravascular electrode in the superior vena cava region, both of these electrodes forming one pole in the shock delivery circuit, and a further intravascular electrode is located in the right ventricle of the heart, forming the other pole.

As already mentioned, patch electrodes of different types have been proposed. U.S. Pat. No. Re 27,757 discloses an early attempt to combine an intravascular electrode and a patch electrode. The patch electrode described therein has a flat plate placed epicardially, sutured under the skin of the anterior chest wall or placed on the surface of the chest. However, there is no teaching in this publication as to how a flat plate sutured under the skin, or even epicardially placed, might be constructed to withstand the movements of the body at such electrode locations over a long period of time.

In contrast, in current and practically used epicardial as well as subcutaneous patch electrodes, flexibility is recognized to be essential. Typically, therefore, they consist of a metallic mesh surface on the side of the electrode facing the heart and an electrically insulating silicon backing on the other side in order that the electrode be flexible enough to accommodate the "wringing" action of the heart and the stretching and contracting actions of the skin, respectively.

SUMMARY OF THE INVENTION

The present invention is based on the perception of the inventors that a new combination of non-epicardial patch electrode placement, size and form lessens the flexibility requirement on the electrode and allows for a more efficient defibrillation and a less complicated implantation and explantation of the electrode than with the currently used subcutaneous flexible patch electrodes. As will be set out below in this description, the invention is also advantageous in other aspects with respect to known patch electrodes.

Essentially, the inventive electrode is characterized by a shape and size as to be locatable between periost and bone at the inner side of a rib which is proximal to the heart of a patient, and further by an electrode fixation means adapted for fixing the electrode to the rib.

This arrangement is, as mentioned, advantageous in several respects over known subcutaneous patch electrodes.

Electrically, the subcostal electrode according to the invention provides for a large conductive electrode surface with a maximum of heart proximity outside the thoracic cavity. In addition, the electrode is advantageous in that the rib does not electrically "shadow" the electrode when defibrillation from the implantable defibrillator system occurs, nor does the electrode present an intercostal "block" to a (emergency shocking) pulse delivered from an external defibrillator as may be applied under emergency conditions. Further, the electrically insulating pad or backing material (such as silicone) associated with conventional patch electrodes can be reduced or totally avoided, as the bone of the rib will provide at least part of the insulating backing for the inventive electrode.

The reduced amount of backing material for the electrode is further advantageous with respect to patient comfort as the amount of material which is foreign to the body can be kept to a minimum.

Mechanically, the subcostal electrode of the invention is advantageous in that it can be securely anchored to and supported by the rib, which is a structure of the body with a minimum of movement compared to subcutaneous tissue. This reduces the strain on the electrode caused by body movement and/or allows for reduced flexibility requirements on the electrode. Also, the risk for dislocation or "wandering" of the electrode is reduced.

With regard to implantation, the electrode according to the invention, which in this respect is similar to conventional, subcutaneous patch electrodes, can be implanted under local anaesthetic and does not require a thoracotomy or other invasion (such as a subxiphoidal approach) of the patient's chest cavity. However, in contrast to such known patch electrodes, the inventive electrode can further reduce the risk for complications because due to the subcostal location the rib is exposed to the electrode, and the rib is less sensitive to, for example, pain and foreign objects than the skin and the subcutaneous tissue. Further, the subcostal location avoids possible damage to underlying blood vessels and nerves. Also, when closing the incision in the skin with sutures, the electrode, at least in part by its own geometry, will be fixed between the periost and the bone of the rib.

The advantages associated with the implantation of the inventive electrode apply equally to situations where the electrode must be explanted and/or replaced.

Further advantages of the inventive electrode will be set out in connection with specifically claimed and/or described embodiments thereof.

DESCRIPTION OF THE DRAWINGS

A better understanding of the invention may be had from the following description in which exemplifying embodiments of the invention are described in conjunction with the accompanying drawings, wherein like reference numerals refer to like components, and where:

FIG. 1 is a side view of a first embodiment of the inventive electrode,

FIG. 2 is a horizontal view of the inventive electrode according to FIG. 1,

FIG. 8 is a side view of a second embodiment of the inventive electrode, and FIG. 9 is a side view of a third embodiment of the inventive electrode.

FIG. 10 is a view of an end of the inventive electrode, showing an alternative version of elements for fixing the electrode to a rib.

FIG. 11 is a side elevational view of a further, alternative fixing element in the form of a clip.

DESCRIPTION OF THE PREFERRED EMBODIMENTS

Figure 6:
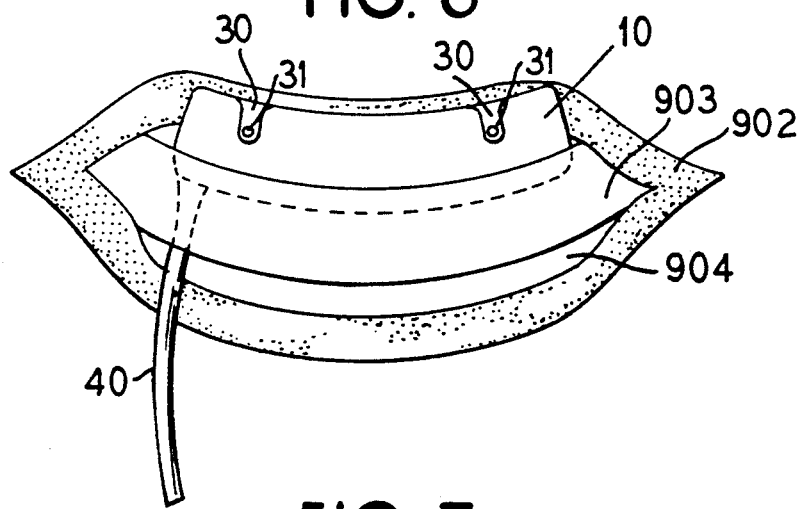
Figure 7:
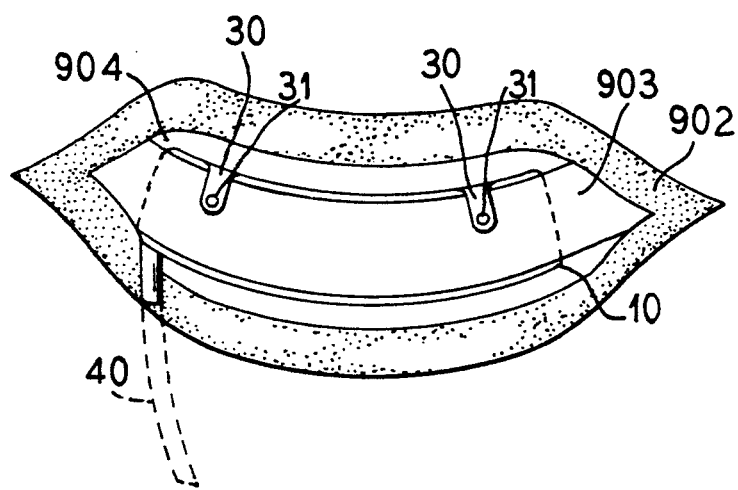

FIG. 1 shows a side view of a first embodiment of a defibrillation electrode 10 according to the invention. The electrode 10 is formed in a substantially elongated, rectangular configuration with side dimensions ranging from approximately 2–15 cm in length and 2–5 cm in width. Preferably, the electrode 10 is approximately 5×2 cm. The actual electrode element is a sheet 20, preferably resilient. The sheet 20 may be formed of metal, such as titanium or platinum, or any other electrically conductive, implantable material. Referring to FIG. 2, the sheet 20 has an inner side 21 facing the heart and an outer side 22 facing a supporting and anchoring rib (FIGS. 6 and 7). The thickness of the sheet 20 should be sufficient to provide structural strength against kinks in the sheet 20 during implantation of the electrode 10, and also sufficient to meet the electrical requirements associated with defibrillation. Any upper edge 23 of the sheet 20 is provided with a plurality of anchoring or fixing elements, such as tags 30, preferably integral thereto and preferably two in number as shown in FIGS. 1 and 2. Each tag 30 may have an opening 31. Alternatively, the fixing elements may be separate elements in the form of a clip 36 as shown in FIG. 11 enclosing the upper part of the rib and the electrode 10 and preferably comprised of resilient, electrically conductive or non-conductive, material for anchoring the electrode 10 to the rib by snap-action. One of the inner side 21 or the outer side 22 of the sheet 20 (preferably the inner side 21) is connected to a suitable energy source for defibrillation through an insulated lead 40 having a central conductor 41 connected to the sheet 20 at a low resistance joint 42. The energy source and its connection to the lead 40 will not be further described as they are well-known and do not form part of the invention.

FIGS. 1 and 2 show the electrode 10 slightly curved, indicating its geometrical shape after implantation. This geometrical shape is selected to be in conformity with that of the chest-cavity form, and thus essentially cylindrical, following the inner periphery of the anchoring rib. The electrode 10 may be formed into this geometrical shape by the surgeon during implantation. Alternatively, the rib-like geometrical shape of electrode 10 may be prefabricated. Although not shown the electrode 10 may be provided with further dislocation inhibiting means, such as protrusions in the sheet 20, the tips of the protrusions being placed on the rib-facing side of the sheet 20, for better anchoring the electrode 10 to the rib in cooperation with the aforementioned means.

Figure 3:
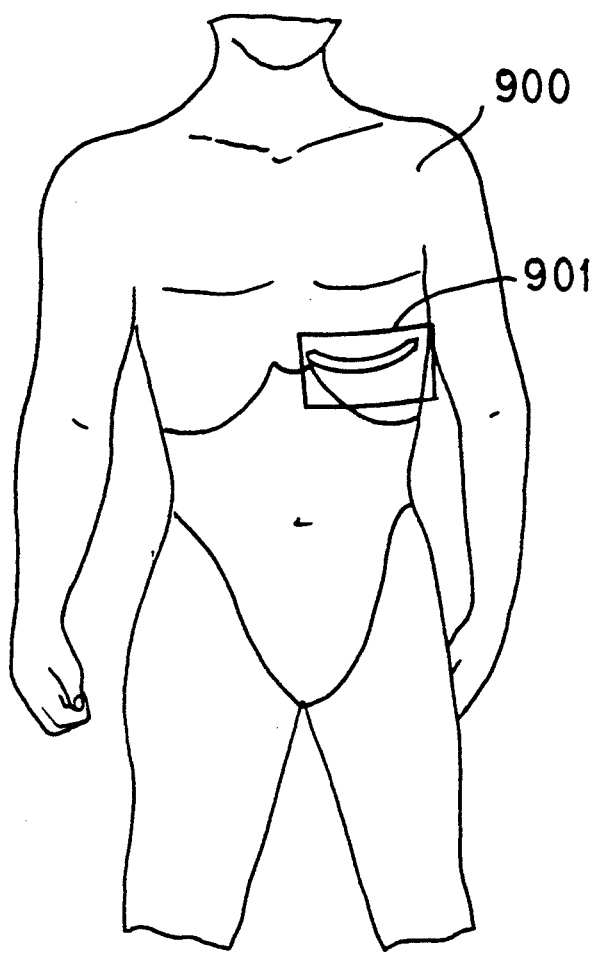
FIG. 3 illustrates the chest contour and the incision location of a patient which is about to have the inventive electrode of FIG. 1 implanted, FIGS. 4 to 7 respectively illustrate different steps in the implanting procedure for the electrode in FIG. 1.
Figure 4:
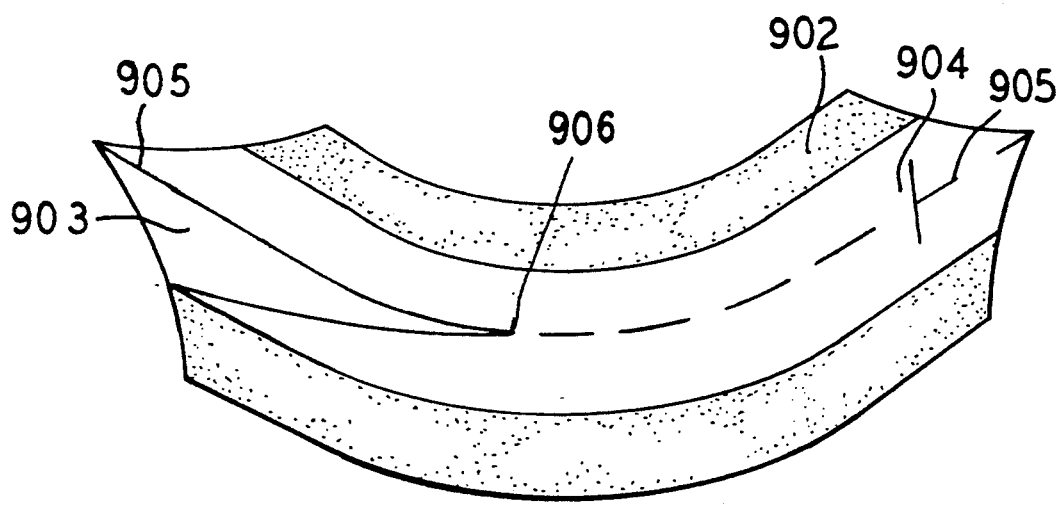

The procedure for implanting the electrode 10 may be as follows. Referring to FIG. 3, the contour of the chest cavity of a patient 900 is shown and the incision location is shown as a rectangular area 901. The rectangular area 901 is shown enlarged in FIG. 4. A skin incision is made to expose a rib with respect to surrounding tissue 902 (shaded areas in FIGS. 4 to 7), the rib being suitably located with respect to the heart for defibrillating purposes, such as the fourth rib. Still referring to FIG. 4, the bone 903 of the exposed rib is separated on its outer side from the periost 904 by means of a suitable tool, such as a dissector, after an incision through the periost 904. The incision is made along the centerline 905 of the rib, this centerline 905 being shown as a dashed line prior to incision and shown solid following incision, the point of incision being indicated at 906.

Figure 5:
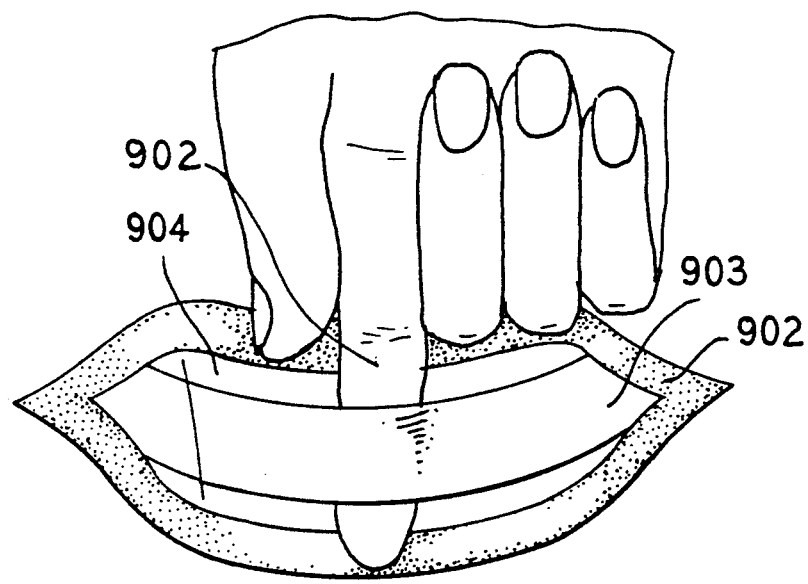

FIG. 5 illustrates the separation of the bone 903 from the periost 904 on the inner side of the rib by means of a finger 907. The electrode 10 may now be formed and inserted (FIG. 6) into the space created between the periost 904 and the inner or subcostal side of the bone 903 until the tags 30 become hooked on the upper edge of the bone 903. FIG. 7 shows the electrode 10 fully inserted and fixed against the bone 903 by means of the tags 30, which are bent to an extent so that they become engaged against the bone 903. Holes 31 may be used as an additional means for securing the electrodes 10 to the bone 905, the holes 31 then being used in combination with sutures (not shown) around the bone 905. Alternatively, if the sheet 20 and the tags 30 are formed from resilient material, the tags 30 may be biased against the outer side 22 of the electrode 10. The tags 30 are then slightly bent open to allow the electrode 10 to be inserted with respect to the bone 905. When the electrode 10 is fully inserted, the tags 30 are released, engaging and securing the electrode 10 to the bone 905 by snap-action. When the electrode 10 has been fixed to the bone 903, the skin incision is sutured while the incision in the periost 904 might be left unsutured and separated from the bone 903. The electrode 10 will remain in place in the interspace between the periost 904 and the bone 903 due to its geometrical shape, which is in conformity with the rib.

FIG. 8 shows a side view of a second embodiment of the electrode 10, differing from that in FIG. 1 only in that the tags 30 are not provided and instead a plurality of openings 31 have been located along the upper and lower edges of the sheet 20. The electrode 10 of this second embodiment is implanted in accordance with the procedure previously described with the exception that instead of securing the electrode 10 to the bone 903 by the tags 30, the holes 31 are employed for anchoring the electrode 10 to the bone 903 by means of sutures, such as suture 32. Also, the electrode 10 in this embodiment may be provided with auxiliary anchoring means in the form of protrusions 37 in the sheet 20. Instead of sutures or in cooperation therewith, the electrode 10 can be anchored to the rib by means of such snap-action clips as already mentioned.

FIG. 9 shows a side view of a third embodiment of the electrode 10. In this embodiment, the electrically active part or centrally located inner surface of the electrode 10 is comprised of a mesh 25 of a material such as titanium. The mesh 25 is embedded in a relatively thin backing pad 26 of electrically insulating and mechanically supporting material, such as silicone. The pad 26 has several tags 30, each possibly having one or more openings 31, along its upper edge, and possibly also along its lower edge. The electrode 10 is implanted as previously described, with the exception that the electrode 10 now remains secured to the bone 903 with the tags 30 which are part of the pad 26. The mechanical properties of the insulating pad 26 should be similar to those of the previously described sheet 20. In order to give the pad 26 a suitable mechanical structure, a material such as Dacron ® might be incorporated into the pad 26. Alternatively or additionally, the mesh 25 may be arranged sufficiently large to cover most of the pad 26 including the tags 30, the perimeter of the mesh 25 then being covered at the front, heart proximate side with an insulating layer of a material such as silicone. Also the electrode 10 in this embodiment may be provided with auxiliary anchoring protrusions 37 (in the pad 26) as described previously. Also, the previously mentioned clips can replace the tags 30.

The sheet 20 and the tags 30 in the first and the second embodiments may also be provided with a thin, electrically insulating backing layer to improve the electrical, insulating properties of the electrode 10. The tags 30 may be provided with such a layer on both sides. The layer may be a material such as silicone or an oxidized layer of the sheet 20.

Although the electrode of the invention has been described in the illustrated embodiments to be made of certain materials, such as titanium, it is noted that the inventive electrode is not limited thereto. Any implantable conductive material may be used and it is contemplated that, for instance, shape-memory metal might be employed in order to facilitate implantation/forming/fixation of the electrode by the surgeon. Also the body fixation means described in the specific embodiments, such as sutures and tags, are examples only and are not intended as the exclusive types of fixing means which can be used. Other fixing means can be used in addition to those described, either as substitutes or in cooperation therewith. Such additional fixing means between the bone and the electrode may comprise hook-and-loop fasteners 35 (FIG. 10) (Velcro ®) one layer of which is carried at each of overlapping tags 30, glue, 34 (FIG. 2) on an underside of the tags 30 screws 33 (FIG. 8) and press buttons.

Finally, it is noted that the electrode of the invention can be implanted not only at a single rib, but also a selected number of ribs may each be provided with one or more electrodes.

Although further modifications and changes may be suggested by those skilled in the art, it is the intention of the inventors to embody within the patent warranted hereon all changes and modifications as reasonably and properly come within the scope of their contribution to the art.

We claim as our invention:

1. An electrode for implantation in a patient and for connection through a lead to a heart stimulation/sensing system, said electrode comprising an active electrode element of conductive material and having a shape and size conforming to an interspace between the periost and the bone at the inner side of a rib proximal to the heart of said patient for locating said electrode at said interspace, and having fixing means for fixing said electrode element to said rib.

2. An electrode according to claim 1, wherein said shape of said electrode is substantially an elongated rectangle, which is slightly curved along its length to be in conformity with said rib having chest-cavity form.

3. An electrode according to claim 1 wherein said size of said electrode is that of a length between approximately 2-15 cm and a width between approximately 2-5 cm.

4. An electrode according to claim 3, having a length of substantially 5 cm and a width of substantially 2 cm.

5. An electrode according to claim 1 wherein said size of said electrode in width is substantially that of said rib.

6. An electrode according to claim 1 wherein said fixing means is integral with said electrode element.

7. An electrode according to claim 6 wherein said fixing means is included in the shape and the size of said electrode.

8. An electrode according to claim 6 wherein said fixing means includes a plurality of tags disposed at least along an upper edge of said electrode.

9. An electrode according to claim 6 wherein said fixing means is provided with openings.

10. An electrode according to claim 6 wherein said electrode further has auxiliary fixing means, cooperating with said fixing means, for assisting said fixing means in fixing said electrode element to said rib.

11. An electrode according to claim 10, wherein said auxiliary fixing means is a plurality of protrusions extending from said electrode element with tips of said protrusions being disposed on a side of said electrode proximate to the inner side of said rib.

12. An electrode according to claim 1 wherein said fixing means includes at least one element separate from said electrode element.

13. An electrode according to claim 12, wherein that said at least one element is an element selected from the group consisting of screws, hook-and-loop fasteners, glue and snap-action clips.

14. An electrode according to claim 12 wherein said electrode further has auxiliary fixing means, cooperating with said fixing means, for assisting said fixing means in fixing said electrode element to said rib.

15. An electrode according to claim 14, wherein said auxiliary fixing means is a plurality of protrusions extending from said electrode element with tips of said protrusions being disposed on a side of said electrode proximate to the inner side of said rib.

16. An electrode according to claim 1 wherein said active electrode element of conductive material is formed of material selected from the group consisting of titanium, platinum and shape-memory metal.

17. An electrode according to claim 1 wherein said active electrode element is a sheet.

18. An electrode according to claim 1 wherein said active electrode element is a mesh.

19. An electrode according to claim 1 further comprising an electrically insulating layer at least partially covering said active electrode element.

20. A method for implanting an electrical stimulation electrode in a patient comprising the steps of:

making a cutaneous incision to expose a rib, and surrounding tissue including the periost, along a longitudinal direction of said rib;

separating the bone of said rib from the periost to create an opening between the bone and the periost at an inner side of said rib;

inserting an electrical stimulation electrode in said opening; and fixing the position of said electrode in said opening relative to said bone.

21. A method as claimed in claim 20 wherein the step of exposing said rib is further defined by exposing the fourth rib.

* * * * *